United States Patent [19]
Hosaka et al.

[11] Patent Number: 6,084,151
[45] Date of Patent: Jul. 4, 2000

[54] METHOD OF PRODUCING A MINI-POTATO

[75] Inventors: Kazuyoshi Hosaka, Kasai; Kuniyoshi Kishimoto, Kakogawa; Shiro Kuge; Hirokazu Hashizume, both of Kasai, all of Japan

[73] Assignee: President of Kobe University, Kobe, Japan

[21] Appl. No.: 09/106,848

[22] Filed: Jun. 30, 1998

[30] Foreign Application Priority Data

Oct. 31, 1997 [JP] Japan ................................ 9-299888

[51] Int. Cl.$^7$ .............................. A01H 1/00; A01H 1/02; A01H 1/04
[52] U.S. Cl. ..................... 800/269; 800/260; 800/317.2
[58] Field of Search .................................. 800/200, 260, 800/269, 317.2

[56] References Cited

FOREIGN PATENT DOCUMENTS 0 574 283 A1   12/1993   European Pat. Off. .
WO 88/04137    6/1988    WIPO .

OTHER PUBLICATIONS

Database FSTA International Food Information Service (IFIS), Frankfurt/Main, DE. Quiros C F et al: "Biochemical and Folk Assessment of Variability of Andean Cultivated Potatoes".

Data Cab, Cab International, Wallingford, Oxon, GB AN—95:156499, Ranalli, P: "Microtuber and Minituber Production and Field Performance Compared with Norman Tuber".

Principles of Cultivar Development. Walter R. Fehr. McGraw–Hill, Inc. United States. p. 379, 1987.

The Production of New Potato Varieties: technological advances, edited by G.J. Jellis & D.E. Richardson, Cambridge University Press, NY, pp. 1,11,15,32,95, 172–177, 229, 231, 240, 242–243,248, 332, 1987.

Production and Performance of Potato Mini—tubers. B.S. Ahloowalia, Euphytica, 75 (3), pp. 163–172, 1994.

*Primary Examiner*—David T. Fox
*Assistant Examiner*—Anne Marie Grünberg
*Attorney, Agent, or Firm*—Oblon, Spivak, McClelland, Maier & Neustadt, P.C.

[57] ABSTRACT

*Solanum stenotomum*, *Solanum phureja* and *Solanum goniocalyx*, which are diploid potatoes native to the Andes, are crossed by open pollination, thereby forming a hybrid population rich in genetic variation. The hybrid population is raised while screening the hybrid population on the basis of selection criteria including a yield thereof, thereby reconstituting the hybrid population. The reconstituted hybrid population is raised for seedlings under short-day light conditions while limiting a rhizosphere thereof and controlling the growth at a slightly lower temperature during a potato-tuber growing period. A mini-potato edible whole (including skin) in one bite can be thus obtained.

4 Claims, No Drawings

METHOD OF PRODUCING A MINI-POTATO

BACKGROUND OF THE INVENTION

The present invention relates to a novel potato species capable of providing a mini-potato, which is a mini-tomato-size potato and edible whole (including rind on skin) in one bite, and a method of producing the mini-potato by raising the novel potato species.

Hitherto, growing large farm products has been a basic strategy in the agricultural field. In contrast, small farm products were evaluated and treated as low grade products. However, since eating habits have changed in recent days, the small farm products are rather valued in some cases. A mini-tomato edible in one bite is a representative example of successful small farm products. However, not so many successful small farm products other than the mini-tomato are known at present.

With respect to potatoes, a mini-tomato-size potato which is edible whole (including rind on skin) in one bite, has not yet been produced. Potatoes are therefore usually peeled, cut into an appropriate size, and then cooked. In the case of a baked potato, the potato is cooked (baked) and then cut into bite-size pieces at the table. Although immature potato tubers (about 30 g weight) called "small potato" can be produced when a potato plant is grown in a general cultivation method, the size of the small potato is still too large to be used whole in snack foods.

Then, if it is possible to produce such a mini-potato edible whole (including skin) in one bite, similarly to the mini-tomato, the mini-potato will be valuable as a raw food material for snack confectioneries and as snacks taken with beer.

BRIEF SUMMARY OF THE INVENTION

An object of the present invention is to provide a method of producing a mini-tomato-size potato called a mini-potato which is edible whole (including skin) in one bite.

The object described above is achieved by the method of producing a bite-size mini-potato comprising the steps of:

crossing Solanum stenotomum, *Solanum phureja* and *Solanum goniocalyx*, which are diploid potatoes native to the Andes, by open pollination, thereby forming a hybrid population rich in genetic variation;

effecting breeding cultivation of the hybrid population and screening the hybrid population on the basis of selection criteria including a yield thereof, thereby reconstituting the hybrid population; and effecting seedling cultivation of the reconstituted hybrid population to obtain seeds, the seedling cultivation being effected under short-day light conditions while limiting a rhizosphere and controlling the growth at a slightly low temperature during a potato-tuber growth period.

DETAILED DESCRIPTION OF THE INVENTION

In the present invention, diploid species, *Solanum stenotomum, Solanum phureja,* and *Solanum gonicalyx* are used as starting species. This is because the potatoes produced from these diploid species are smaller than those from an ordinary species (tetraploid) and therefore suitable for forming a new species for the mini-potato. A first population is formed by performing open pollination among the three species. This is because it is rather better to screen a potato species starting from a population rich in genetic variation in order to make the best of various shapes and colors of the first population in the resultant food material. When the novel potato species of the present invention is formed, the population is reconstituted by repeating the crossing (bulk-pollen mixed pollination) and screening. This is made to eliminate unpreferable traits (particularly an acrid taste).

In the mini-potato producing method of the present invention, a rhizosphere is limited. This is made to obtain small potato-tubers easily. To limit the rhizosphere, a pot and a culture tray is used.

In the method of the present invention, the seedling cultivation of the hybrid population is effected under short-day light conditions. This is because the potato-tubers of the diploid species is are initiated under the short-day conditions. However, if the diploid species is grown under long-day conditions, an aboveground portion of the potato plant grows well but the potato-tubers underground do not grow. The short-day conditions used herein correspond to the conditions under a natural day-length of autumn to winter.

Growth of the potato plant is controlled at a slightly lower temperature ranging from 20° C. to 5° C., and more preferably at about 10° C. during the potato-tuber growing period. In this case, it is necessary to use an unheated glass house or a vinyl house in order to prevent frost damage.

Now, the present invention will be explained in detail with reference to the following example.

EXAMPLE

A novel potato species of the present invention was produced and then the mini-potato was obtained by growing the seeds of the novel potato species, as follows.

(1) The Formation of Population

Diploid species (1430 individuals, in total) from the following potato species native to the Andes were planted at random in a cultivated field. Seeds were obtained by open pollination and used as a starting population.

Solanum stenotomum:
  45 individuals taken from each of 14 families
Solanum phureja:
  25 individuals taken from each of 27 families
Solanum goniocalyx:
  25 individuals taken from each of 5 families (II) Breeding Three cycles of selection were carried out to reconstitute the aforementioned population and form a population capable of producing, in as large an amount as possible, a mini-tomato-size mini-potato without an acrid taste while maintaining genetic diversity in shape and color. The selection process will be explained.

First Selection

1992
September 15: Gibberellin treatment of the seeds
  Seeds were immersed in 2000 ppm gibberellin GA 3, overnight.
September 16 : Sowing the seeds
October 5 to 10: Transplanting
  Individuals (1729) were transplanted in a black poly-pot (10.5 cm diameter) and grown by ordinary manners in an unheated glass house.
1993
January 14–18: Harvesting of potatoes
  Potatoes were harvested from each of 1591 individuals.
January 28: Selection
  The harvested potatoes were checked and selected in accordance with selection criteria* described later. 438 individuals were selected.

* The selection carried out on January 28 was made by discarding individuals which produced potatoes satisfying the following conditions.

March 2: Planting ubers

Unsprouted 183 individuals were planted in a heated greenhouse.

April 1 to 9: Transplanting 126 emerged individuals were transplanted to 6 inches clay pots and placed in an unheated screen house.

May 14 to 21: Pollination

Pollen was collected from 109 blooming individuals to make a pollen mixture. 544 flowers in total were pollinated with the pollen mixture.

June 18–24: Collecting berries 390 berries were collected. One month later, seeds were extracted from the harvested berries.

(1) Individuals whose buds have already extended;
(2) Individuals producing extremely small potatoes alone;
(3) Individuals whose products have deep eyes;
(4) Individuals whose products (potatoes) are not uniform in size;
(5) Individuals whose products (potatoes) have unacceptable shapes;
(6) Individuals whose yield is low compared to others;
(7) Individuals whose products have still clear stolon-end portions.

Second Selection

1993

September 8: Gibberellin treatment of the seeds

Seeds obtained in the first selection were immersed in 2000 ppm gibberellin GA 3, overnight.

September 9: Sowing seeds

September 24–27: Transplanting

Individuals (2881) were transplanted in a black poly-pot (10.5 cm diameter) and grown by ordinary manners in an unheated glass house.

1994

January 5–6: Harvesting of potatoes

Potatoes were harvested from each of 2442 individuals.

January 12–13: Selection

The harvested potatoes were checked and selected in accordance with the same selection criteria* as used in the first selection test. 719 individuals were selected.

Late in January: Taste test

One potato was taken from each of the individuals, steamed and tasted. As a result, 365 potatoes presenting no acrid taste were selected.

March 2: Planting tubers 201 unsprouted individuals were planted in a heated greenhouse.

March 31: Transplanting 127 emerged individuals were transplanted to 6 inches clay pots and grown by ordinary manners in an unheated screen house.

May 9 to 19: Pollination

Pollen was collected from 121 blooming individuals to make a pollen mixture. 290 flowers in total were pollinated with the pollen mixture.

June 18–24: Collecting berries 203 berries were collected. One month later, seeds were extracted from the harvested fruits.

Third Selection

1994

September 5: Gibberellin treatment of the seeds

Seeds obtained in the second selection were immersed in 2000 ppm gibberellin GA 3, overnight.

September 6: Sowing seeds in cell trays

October 12–24: Transplanting

Individuals (1800) were transplanted in a black poly-pot (10.5 cm diameter) and grown by ordinary manners in an heated glass house.

1995

January 9–10 Harvesting of potatoes

Potatoes were harvested from each of 1772 individuals.

January 25–26: Selection

The harvested potatoes were checked and selected in accordance with the same selection criteria* as used in the first selection. 465 individuals were selected.

February 20: Taste test

One potato was taken from each oh 339 unsprouted individuals steamed, and tasted. As a result, 240 potatoes without an acrid taste were selected.

March 7: Planting tubers 162 unsprouted individuals were transplanted in a heated greenhouse.

March 28–April 10: Tlansplanting 139 emerged individuals were transplanted to 5 inches clay pots and grown by ordinary manners in an unheated screen house.

May 9 to 23: Pollination

Pollen was collected from 121 blooming individuals to make a pollen mixture. The 644 flowers were pollinated with the pollen mixture.

June 12–23: Collecting berries

Berries (252) were collected. One month later, seeds were extracted from the harvested berries.

(III) Cultivation Test

Potato plants were planted in a culture tray (510×365×82 mm) at three different densities: As a "dense plot", 20 potato plants were planted per tray. As an "ordinary plot", 15 potato plants were planted per tray. As a "sparse plot", 8 potato plants were planted per tray. The density in the ordinary plot corresponds to that of the aforementioned selection tests. One test plot consists of 24 trays. The same cultivation test was repeated three times and the yields thereof were compared. The cultivation was performed as follows:

1996

September 2: Gibberellin treatment of the seeds

Seeds obtained in the third selection were immersed in 2000 ppm gibberellin GA.3, overnight.

September 6: Sowing seeds in cell trays

October 12–24: Transplanting

Individuals (3096) were planted in 216 culturing trays in total and grown by ordinary manners in an unheated glass house.

1997

January 16–17: Harvest of potatoes

Potatoes were harvested independently in three densing plots.

In the aforementioned cultivation test, the yields (kg) of the potatoes per plot (24 culturing trays) which is classified by size were as follows. The size classification of the potato was made using sieves of 1.5 cm mesh and 4.0 cm mesh. More specifically, the potato passing through the 1.5-mesh sieve was regarded as an "extremely small potato". The potato remaining on the 4.0-mesh sieve was regarded as an "extremely large potato". A "mini-potato" was one which can pass through the 4.0-mesh sieve and remain on the 1.5-mesh sieve.

| District | Repli-cate | Potato Size | | |
|---|---|---|---|---|
| | | Mini-potato | Extremely large | Extremely small |
| High density plot | 1 | 8.80 | 0.17 | 0.85 |
| | 2 | 8.80 | 0.19 | 0.72 |
| | 3 | 8.28 | 0.15 | 0.80 |
| | Average | 8.63 | 0.17 | 0.79 |
| Ordinary plot | 1 | 7.43 | 0.38 | 0.79 |
| | 2 | 7.46 | 0.21 | 0.92 |
| | 3 | 5.98 | 0.0 | 1.01 |
| | Average | 6.96 | 0.20 | 0.97 |
| sparse plot | 1 | 4.64 | 0.05 | 0.76 |
| | 2 | 5.36 | 0.20 | 0.36 |
| | 3 | 6.65 | 0.19 | 0.40 |
| | Average | 5.55 | 0.15 | 0.51 |

As is apparent from the aforementioned results, the yields of the mini-potato in the cultivation described above were about 80% or more. In particular, the mini-potato was obtained at a high yield in the dense plot.

According to the present invention as detailed in the foregoing, it is possible to obtain a mini-potato edible whole (including skin) in one bite. Therefore, a useful food material suitable for snack confectioneries and snacks taken with a beer can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A method of producing a bite-size mini-potato comprising the steps of:

crossing *Solanum stenotomum, Solanum phureja* and *Solanum goniocalvx,* which are thereby forming a hybrid population rich in genetic variation;

effecting breeding cultivation of the hybrid population and screening the hybrid population on the basis of selection criteria including a yield thereof, thereby improving the selected characteristics within the hybrid population; and effecting seedling cultivation of the screened hybrid population, thereby obtaining seeds, the seedling cultivation being effected under short-day light conditions while limiting a rhizosphere and controlling the growth at a temperature of 5° C. to 20° C. during the potato tuber growing period.

2. The method according to claim 1, wherein a pot or a culture tray is used as means for limiting a rhizosphere.

3. The method according to claim 1, wherein the controlling of the growth during the potato-tuber growing period is made at about 10° C.

4. The method according to claim 3, wherein controlling the growth at said temperature is performed in an unheated glass house or a vinyl house.

* * * * *